US010499755B2

(12) United States Patent
Aramli (10) Patent No.: US 10,499,755 B2
(45) Date of Patent: *Dec. 10, 2019

(54) BED COVERING APPARATUS EQUIPPED WITH AN AIR INLET THAT HAS A FASTENER FOR SELECTIVELY OPENING AND CLOSING THE AIR INLET

(71) Applicant: BEDJET LLC, Newport, RI (US)

(72) Inventor: Mark Darius Aramli, Newport, RI (US)

(73) Assignee: BEDJET LLC, Newport, RI (US)

( * ) Notice: Subject to any disclaimer, the term of this patent is extended or adjusted under 35 U.S.C. 154(b) by 45 days.

This patent is subject to a terminal disclaimer.

(21) Appl. No.: 15/912,581

(22) Filed: Mar. 6, 2018

(65) Prior Publication Data

US 2018/0192794 A1    Jul. 12, 2018

Related U.S. Application Data

(63) Continuation-in-part of application No. 15/441,217, filed on Feb. 23, 2017, now Pat. No. 9,907,407, which is a continuation-in-part of application No. 14/276,162, filed on May 13, 2014, now abandoned.

(51) Int. Cl.
*A47G 9/02* (2006.01)
*A47G 9/00* (2006.01)
*A61F 7/00* (2006.01)

(52) U.S. Cl.
CPC .......... *A47G 9/0215* (2013.01); *A61F 7/0097* (2013.01); *A47G 2009/003* (2013.01); *A61F 2007/006* (2013.01)

(58) Field of Classification Search
CPC ... A47C 21/044; A47C 21/042; A47C 21/048; A47G 9/02; A47G 9/023; A47G 9/0215; A47G 9/0223; A47G 2009/003; A61G 7/05784; A61G 7/05792; A61F 7/00
See application file for complete search history.

(56) References Cited

U.S. PATENT DOCUMENTS

| 4,660,388 A | * | 4/1987 | Greene, Jr. | ........... | A47G 9/0215 165/46 |
| 4,777,802 A | * | 10/1988 | Feher | .................... | A47G 9/0215 5/423 |
| 5,265,599 A | * | 11/1993 | Stephenson | ........... | A61F 7/0097 165/46 |
| 5,304,213 A | * | 4/1994 | Berke | .................. | A47G 9/0215 607/104 |

(Continued)

*Primary Examiner* — Nicholas F Polito
*Assistant Examiner* — Rahib T Zaman
(74) *Attorney, Agent, or Firm* — Robert J. Hess; Hess Patent Law Firm (57) ABSTRACT

A bed covering having a plurality of layers between which is an air cavity and having at least one air inlet in fluid communication with the air cavity. The layers have folds and have fasteners. The fasteners may fasten and unfasten and include respective fastener components that self-close when brought together to engage each other and that disengage to separate from each other. The fastener components when fastened to each other close the at least one air inlet and when unfastened from each other open the at least on air inlet. An elastic band is also provided on the periphery to wrap around an air tube when inserted into the at least one air inlet and apply an elastic force under tension to retain the same.

13 Claims, 12 Drawing Sheets

(56) References Cited

U.S. PATENT DOCUMENTS

| | | | | |
|---|---|---|---|---|
| 5,336,250 A * | 8/1994 | Augustine | ............ | A47G 9/0215 5/423 |
| 5,384,924 A * | 1/1995 | Dickerhoff | ........... | A47G 9/0215 5/421 |
| 5,405,371 A * | 4/1995 | Augustine | ............ | A47G 9/0215 607/107 |
| 5,675,848 A * | 10/1997 | Kappel | ................ | A47G 9/0215 5/421 |
| 5,728,145 A * | 3/1998 | Phlipot | ................ | A47G 9/0215 607/104 |
| 6,102,936 A * | 8/2000 | Augustine | ................. | A61F 7/00 5/606 |
| 6,119,474 A * | 9/2000 | Augustine | ............ | A47G 9/0215 607/107 |
| 6,168,612 B1 * | 1/2001 | Augustine | ............ | A47G 9/0215 601/16 |
| 6,363,551 B1 * | 4/2002 | Flores | .................. | A47C 21/044 5/421 |
| 7,631,377 B1 * | 12/2009 | Sanford | ............... | A47C 21/044 5/413 R |
| 2003/0145380 A1 * | 8/2003 | Schmid | ................ | A47C 21/044 5/423 |
| 2010/0235991 A1 * | 9/2010 | Ward | ................... | A47C 21/044 5/423 |
| 2011/0289684 A1 * | 12/2011 | Parish | ................. | A47C 21/044 5/421 |
| 2012/0017371 A1 * | 1/2012 | Pollard | ................ | A47G 9/0215 5/423 |
| 2014/0115781 A1 * | 5/2014 | John | ........................ | A47G 9/02 5/492 |
| 2014/0182061 A1 * | 7/2014 | Zaiss | .................... | A47C 21/044 5/423 |
| 2015/0074904 A1 * | 3/2015 | Aramli | ................. | A47C 21/042 5/421 |

* cited by examiner

BED COVERING APPARATUS EQUIPPED WITH AN AIR INLET THAT HAS A FASTENER FOR SELECTIVELY OPENING AND CLOSING THE AIR INLET

REFERENCE TO COPENDING PATENT APPLICATIONS

The present application is a continuation-in-part of application Ser. No. 15/441,217 that was filed Feb. 23, 2017.

BACKGROUND OF THE INVENTION

The invention relates to a bed covering apparatus that has an air inlet equipped with a fastener. In an unfastened condition, the fastener is in a position that leaves open the air inlet. In a fastened condition, the fastener is in a position that closes the air inlet.

The bed covering provides for distribution of a flow of pressurized conditioned air into a zone around the body of a bed occupant. That is, an engineered layer of bedding connects to a supply of pressurized conditioned air evenly distributes the conditioned air to a single specific zone of the bed. There may be connection of one of two independent supplies of conditioned air into the single layer of engineered bedding to evenly distribute such independent supplies into one of two specific dual zone areas about the multiple bed occupants, thus providing independently conditioned zones within the bed for each occupant. The bed covering further avoids the feeling of foreign and unnatural apparatus in the bed to the occupants by providing for a bedding texture against the skin of ordinary cotton linens and comforters.

The body of the average person releases a substantial amount of heat through skin loss and moisture due to perspiration to the surrounding air. The usual practice of covering the body during sleeping has the effect of insulating the body from the surrounding room air and thereby holds such released heat and moisture in the air about the body.

In cold weather when the room temperature may be below 70 degrees F., heavy covering is frequently employed so as to minimize the exchange of air about the body with the surrounding room air and thus has the effect of increasing the air temperature and humidity about the body. In such instances a person will often throw off the covering while asleep, which will then result in chilling. In warm weather when the room temperature is above 70 degrees F., a lighter covering is usually employed but the moisture which results from perspiration is still retained about the body by the insulating covering, causing personal discomfort and results in poor rest.

While air conditioners are highly effective at coarsely controlling the temperature in a room, the customary preference for persons to sleep beneath one or more bed sheets, covers, blankets, etc., coupled with the body's tendency to liberate heat during its normal operation translates to the well-known situation in which the person resting beneath the sheets cannot get comfortable because they are too hot, which is compounded by the proposition that if they remove the covers or sheets from themselves then they become too cold.

Inflatable mattresses have an air inlet opening equipped typically with a plug that is movable between and unplugged position that allows access to the air inlet opening from the outside to effect inflation and a plugged position that closes the air inlet opening in a sealed manner to trap the air inside that inflated the mattress. In the clothing industry, conventional fasteners include snaps, strips of hooks and loops and zippers that are sewn into clothing at a location that is adjacent a clothing opening. In that way, a fastener can be either fastened into a closed position that closes the adjacent clothing opening or unfastened to open the adjacent clothing opening.

A conventional bed covering is not inflatable and for that reason does not have air inlet openings to receive the flow of pressurized air. To the extent that a consumer wants an inflatable bed covering to resemble a conventional bed covering that is not inflatable when the inflatable bed covering is not in use, it would be desirable to at least partially conceal if not fully conceal the air inlet of an inflatable bed covering. Further, there exists a need for an improved system for distributing both warm and ventilated or cool conditioned air throughout a bed into one or two zones, while not introducing elements or textures to the users that were previously foreign to the bed, while also avoiding giving rise to a ballooning effect of the bedding while delivering the pressurized air.

BRIEF SUMMARY OF THE INVENTION

The foregoing and other problems are overcome, and other advantages are realized, in accordance with the presently preferred embodiments of these teachings.

One aspect of the invention provides an inflatable bed covering equipped with at least one air inlet that has at least one fastener that can be selectively positioned between a fastened condition, which closes the opening of the at least one air inlet, and an unfastened position, which opens the at least one inlet to enable access to the opening of the at least one air inlet. An elastic band is also provided on the periphery to wrap around an air tube when inserted into the at least one air inlet and apply an elastic force under tension to retain the same.

Preferably, the at least one air inlet is interconnected with an external apparatus which supplies a pressurized flow of conditioned air, such that the air can be evenly distributed within a zone of a bed and not provide the feeling of "rushing air" to the occupants. The bed covering has a plurality of layers that form folds with an air cavity formed between the layers. The layers terminate into a peripheral region that forms the at least one air inlet, which is in fluid communication with the air cavity. The at least one fastener may be secured to a periphery of the at least one air inlet.

The at least one fastener may be conventional snaps that include respective snap components that snap close with each other in a complementary manner and may become hidden from view within the folds of the plurality of layers after all the respective snap components are snapped closed.

The at least one fastener may be conventional strips of hooks and loops that engage each other upon contact with each other to retain themselves in a closed position and may become hidden from view within the folds of the plurality of layers.

The at least one fastener may be a conventional zipper that closes the at least one air inlet when its slider is pulled across in one direction and opens the at least one air inlet when the slider is pulled in a direction opposite the one direction. The zipper may become partially hidden from view within folds of the plurality of layers with the elastic band helping the shrink the closed air inlet by exerting its elastic tension.

Any type of conventional fastener may be used to close the at least one air inlet provided the conventional fastener self closes on itself when its components are brought together and are readily separated from each other under manual force, but should withstand repeated laundering without breakage or deformation.

BRIEF DESCRIPTION OF THE DRAWINGS

For a better understanding of the present invention, reference is made to the following description and accompanying drawings, while the scope of the invention is set forth in the appended claims.

DETAILED DESCRIPTION OF THE PREFERRED EMBODIMENT

The bed covering of the present invention includes an embodiment to accept two independent flows of conditioned air from external apparatus for even distribution into two independent zones within the bed, thus accommodating two occupants' different bed temperature preferences while simultaneously allowing a single top bedding blanket apparatus to cover both occupants without separation between the occupants. In addition, the bed covering may accept both heated, ambient and cooled air as a means of establishing multiple zones of temperature within a bed.

It is preferred to avoid introducing foreign textures or surfaces in contact with the bed occupants other than those that are already commonly used in existing residential bedding such as cotton, cotton blends, and synthetic microfiber materials. The bed covering preferably allows for sufficiently pressurized airflow into the blanket apparatus to evenly distribute air without a large ballooning effect of the blanket or bed covering.

In accordance with one embodiment of the invention is a lower layer sheet comprised of a cotton, cotton blend, or synthetic microfiber, or other similar material commonly used in residential bedding that has some permeability to air, which is joined to an upper layer sheet of similar material but of tighter weave with a lower natural permeability to air. The joined two layers thus create an interior space for the flow of air by defining the air cavity. The upper layer is arranged in a major surface area contacting relation with the lower layer. The lower layer sheet and upper layer sheet shall be joined by a plurality of joining methods within the air flow area that enables contiguous connection to the air flow stream while preventing ballooning of the blanket apparatus while under natural pressure from the flow of pressurized air. The joining methods arrange joining elements to define a substantially continuous closed path with allowance for an inlet port for pressurized conditioned air.

A differential of permeability as between the upper and lower layers causes substantially more of the flow air to be directed towards the occupants versus out the upper layer, while avoiding unsightly appearance of any holes, apertures or other venting means or textures which would not normally be present in ordinary bedding sheets or comforters. The use of both layers being permeable to air increases the occupants' comfort to a more natural bedding experience while pressurized air is not supplied.

In accordance with another embodiment of the invention another feature of the apparatus is a limited flow zone area, where the pressurized conditioned air is directed to only half or some portion of a bed, while the blanket apparatus still covers the entire bed area.

In accordance with another embodiment of the invention another feature of the apparatus is a dual zone flow area, where one flow area is sealed from the other and both have independent inlets for pressurized conditioned air, thus creating a two zone conditioning system for the bed.

Figure 1:
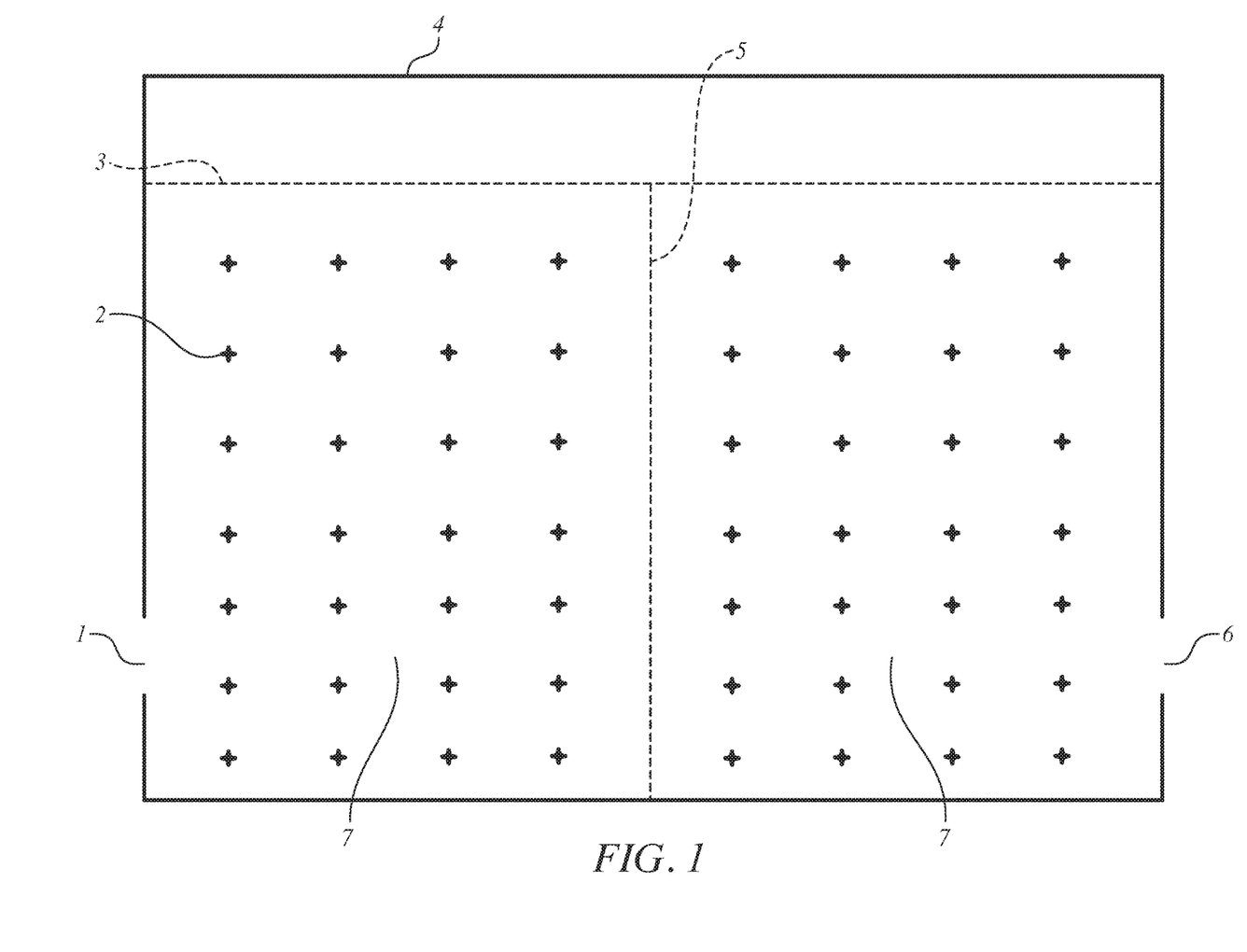
FIG. 1 is a schematic diagram of an exterior view of a blanket in accordance with an embodiment of the invention that distributes conditioned air into zones of a bed.

Referring now to FIG. 1, there is shown a pictorial illustration of an operational use in which the invention is implemented. There is an unsealed area 1 between the upper and lower sheets where a pressurized airflow can be supplied by a hose or other means into the flow area. However, there is a sealed edge 4 between the upper and lower layer sheets. As a consequence of the sealed edge 4, the sealed upper and lower sheets form a flow area 7.

There are a plurality of thread stitches 2 between the upper and lower layer sheets allows open flow paths, but prevents a ballooning effect of the joined sheets from arising when under pressurized airflow. Such a ballooning effect is known from a conventional blanket of FIG. 10. Such a ballooning effect is avoided in accordance with the construction of the blanket in accordance with the invention because of the placement of the thread stitches 2 in a uniform manner in the central region of the blanket. Instead of the thread stitches 2, glue or mechanical fasteners or any form of joining means may be used to join together the upper and lower sheets. The thread stitches 2 may be tack stitches.

An optional sealing line 3 between the upper and lower layers may be provided to further distinguish a smaller zone in the bed that will not need to be inflated. An additional optional sealing line 5 between the upper and lower layers may be provided to create an independent dual zone flow area. The sealing lines 3, 5 may be in the form of a sealing mechanism such as a conventional hook and loop fastener strip that fastens the hooks and loops to each other in a releasable manner.

An additional unsealed area 6 between the upper and lower sheets may be provided for a second independent conditioned flow of air to support the dual zone airflow nature of the apparatus. The unsealed areas 1, 6 constitute ports or access areas for accommodating insertion of ends of air hoses that discharge pressurized conditioned air from a source into the flow area 7.

Figure 2:
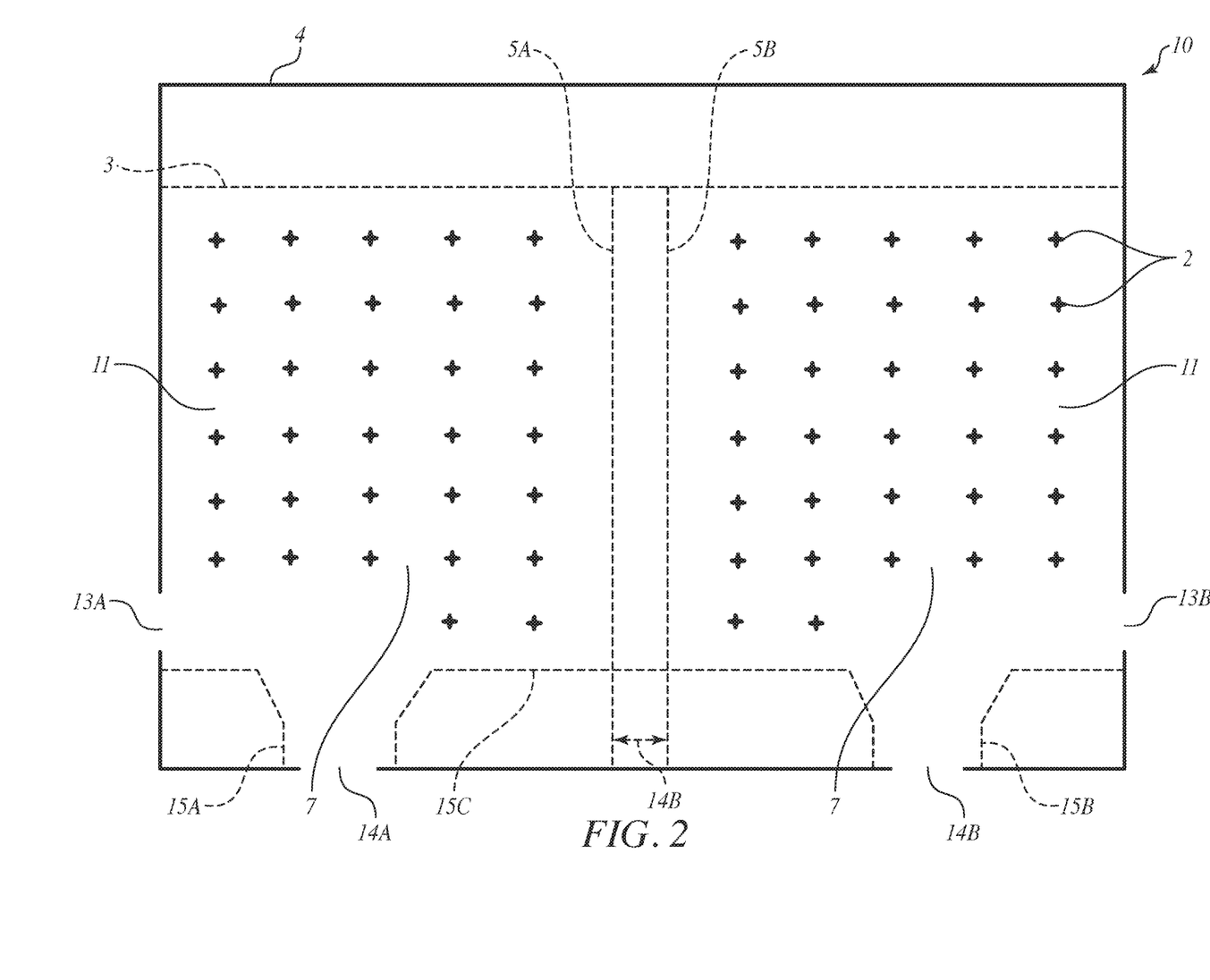
FIG. 2 is a schematic diagram of an exterior view of a non-inflated blanket in accordance with a dual zone embodiment of the invention that distributes conditioned air into zones of a bed.
Figure 3:
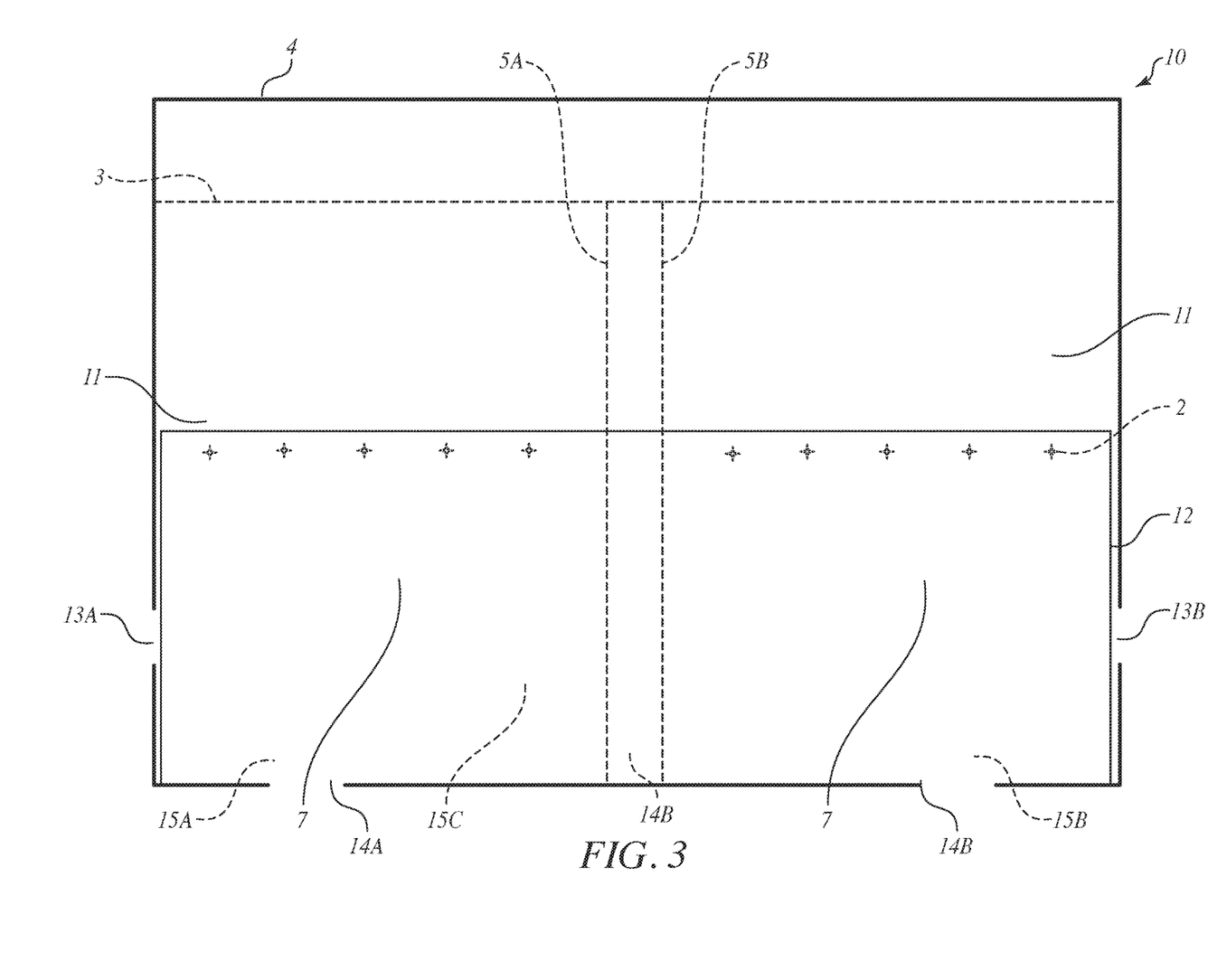
FIG. 3 is a schematic diagram of an interior view of an internal layer of the dual zone embodiment in accordance with the dual zone embodiment of FIG. 2.
Figure 4:
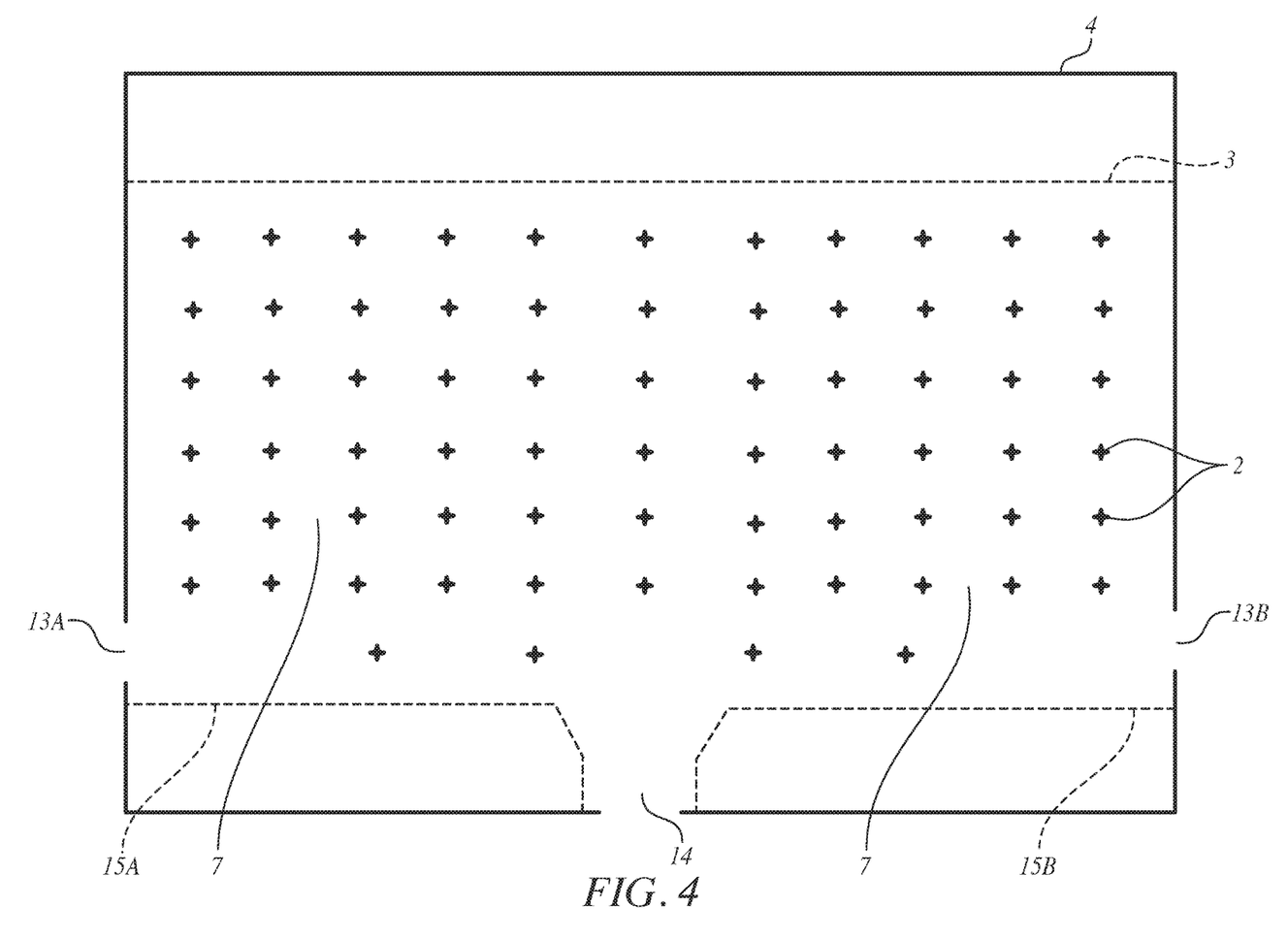
FIG. 4 is a schematic diagram of an exterior view of a non-inflated blanket in accordance with a single zone embodiment of the invention that distributes conditioned air into zones of a bed.
Figure 5:
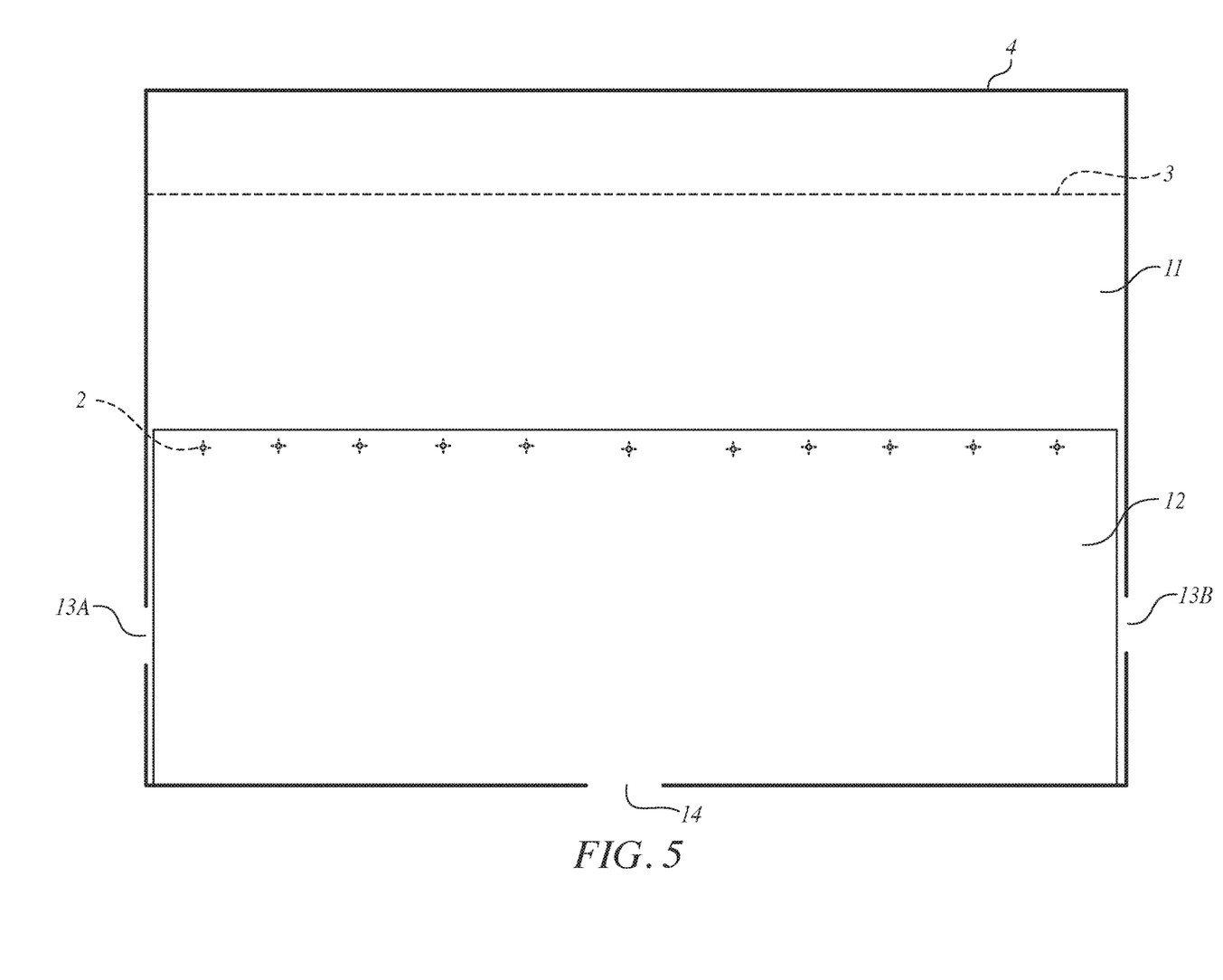
FIG. 5 is a schematic diagram of an interior view of an internal layer of the single embodiment in accordance with the single zone embodiment of FIG. 4.

Turning to the dual zone embodiment of FIGS. 2 and 3 and the single zone embodiment of FIGS. 4 and 5, the blanket 10 has upper and lower sheets 11 with an interior layer 12 between. The interior layer 12 is shorter than the upper and lower sheets 11 and may be sewn onto a bottom portion of the underside of the exterior layer 11 to form a double layer section. The interior layer 12 is also preferably sewn to side and bottom sheet seams and anchored to a bottom row of tack stitches 14.

The upper and lower sheets 11 are preferably of downproof sateen and the interior layer 12 is preferably of percale. The upper and lower sheets 11 are more air permeable than the interior layer 12. As a result, blowing air into the flow area 7 between the upper and lower sheets 11 will result in most of the blown air permeating through upper regions of the upper and lower sheets 11 that are away from the interior layer 12.

There are two sealing lines 5A, 5B in FIGS. 2 and 3 that extend centrally from an optional sealing line 3 to the bottom edge of the upper and lower sheets 11. The sealing lines 3, 5A, 5B may be in the form of a sealing mechanism such as a conventional hook and loop fastener strip that fastens the hooks and loops to each other in a releasable manner. Thus, one may convert the blanket 10 of FIGS. 2 and 3 having dual zones into one having a single zone in the manner of that of FIGS. 4 and 5, except there would still be the two openings 14A, 14B at the bottom as in FIGS. 2 and 3 as opposed to just a single bottom opening 14 as in FIGS. 4 and 5.

It may help to provide for one or more shared or common internal airflow passages that connect the separate internal airflow passages of the dual zones with each other. Such a common internal airflow passage would be open to permit airflow when the separation mechanism 20 is removed and would be closed by the separation mechanism 20 when the separation mechanism 20 is present. Otherwise, inflation may need to arise with one inflation hose extending into either side opening 13A or bottom opening 14A and another inflation hose extending into either side opening 13B or bottom opening 14B.

Additional sealing lines 15A, 15B are provided that extend from the bottom edge of each of the side openings 13A, 13B in a direction inwardly and then turn to run adjacent to respective sides of the bottom openings 14A, 14B. In addition, there is an additional sealing line 15C that run from the remaining sides of the bottom openings 14A, 14B inwardly and the across as shown.

In the case of the blanket 10 being for king size, there are five tack stitches per row on each side joining top and bottom layers, evenly spaced apart from each other starting at the center seam. In the case of the blanket 10 being for a queen size, there are four tack stitches per row on each side instead of five. In the case of the blanket 10 being for double size, there may be three track stitches per row on each side instead of four for the queen size and instead of five for the king size.

Since the dual zone embodiment of FIGS. 2 and 3 has dual zones, each of the zones is provided with its own set of side and bottom openings 13A, 13B, and 14A, 14B. Since the single zone embodiment of FIGS. 4 and 5 has a single zone, there are side openings 13A, 13B, but only a single centrally located bottom opening 14.

The flow areas 7 throughout the blanket become inflated around the thread stitches 2. The thread stitches prevent the full ballooning effect of FIG. 10 from arising after inflating from a deflated condition such as that of FIG. 9. Even though the bottom portion of the blankets of FIG. 2 and FIG. 4 lack tack stitches 2, the enhanced reduction in air permeability afforded by the interior layer 12 of FIG. 3 and FIG. 5 in effect causes the air to flow or migrate under pressure to the upper portion of exterior layer 11 that has greater air permeability.

In the case of the single zone embodiment of FIGS. 4 and 5, the number of tack stitches per row on each "side" is the same as for the dual zone embodiment of FIGS. 2 and 3, except there is an additional tack stitch provided at the center between the two "sides", where arises the central divider space 15 for the dual zone embodiment of FIGS. 2 and 3. Also, the sealing lines 15A, 15B each extend from respective areas adjacent the lower sides of the side openings 13A, 13B inwardly until turning to run adjacent respective sides of the single centrally located bottom opening 14. The sealing lines 15A, 15B (FIGS. 2 and 4) and the sealing line 15C (FIG. 2) may each in the form of common thread stitching.

Figure 6:
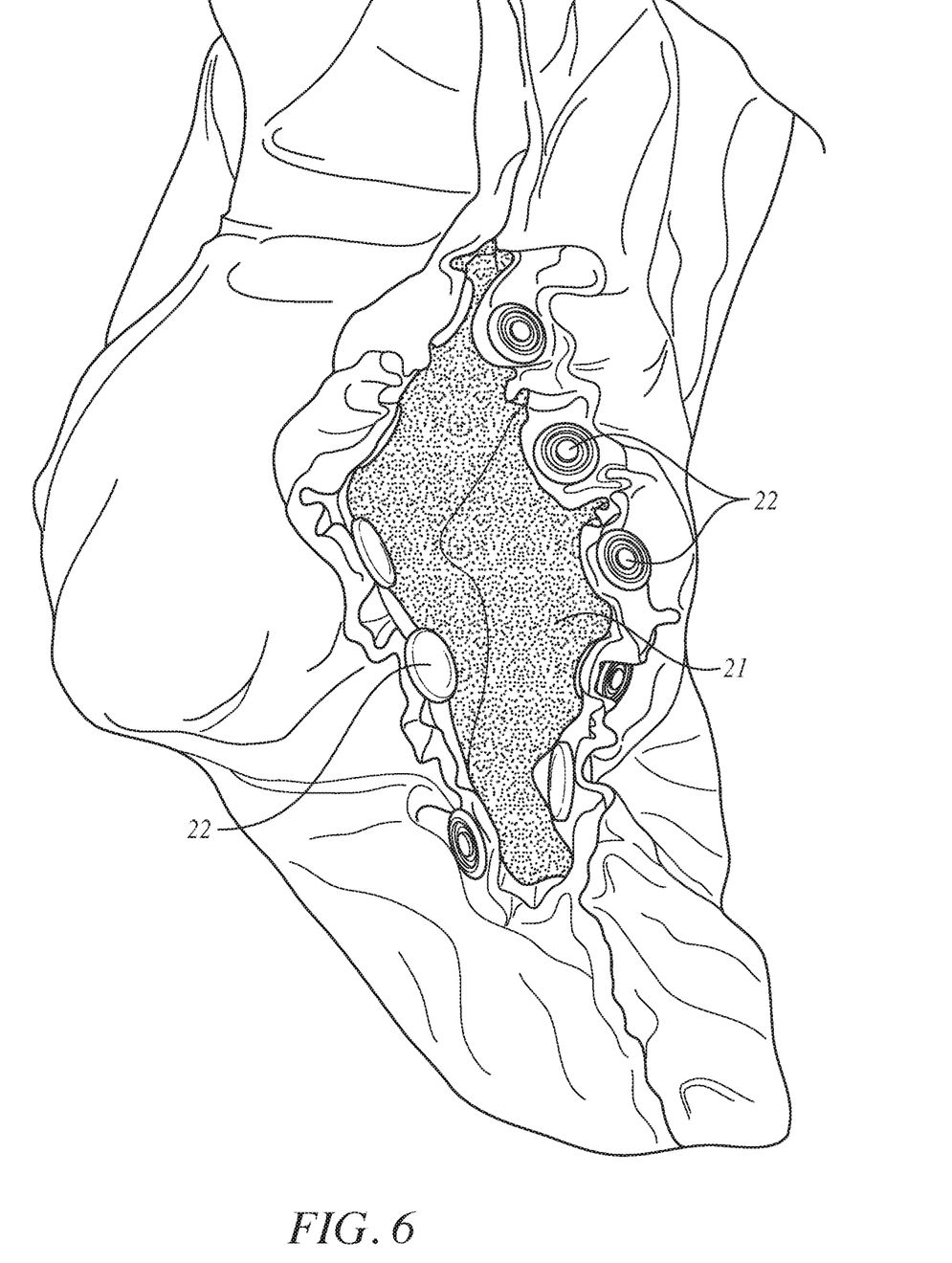
FIG. 6 is an isometric view of a hose seal in an open position accordance with the invention to show snaps about an opening.
Figure 7:
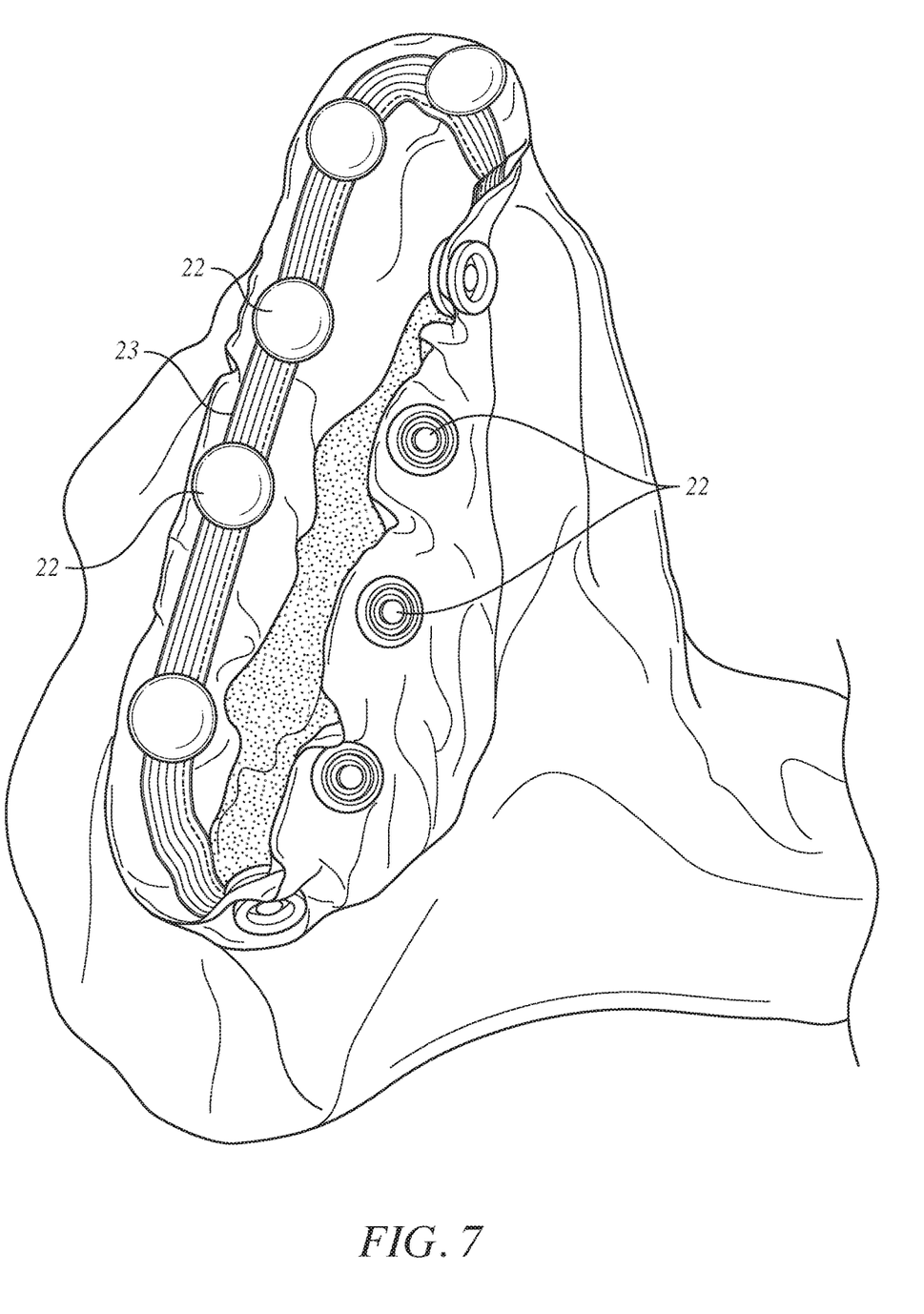
FIG. 7 is an isometric view of a hose seal in the open position accordance with FIG. 7 but turned in a manner to reveal an elastic band.
Figure 8:
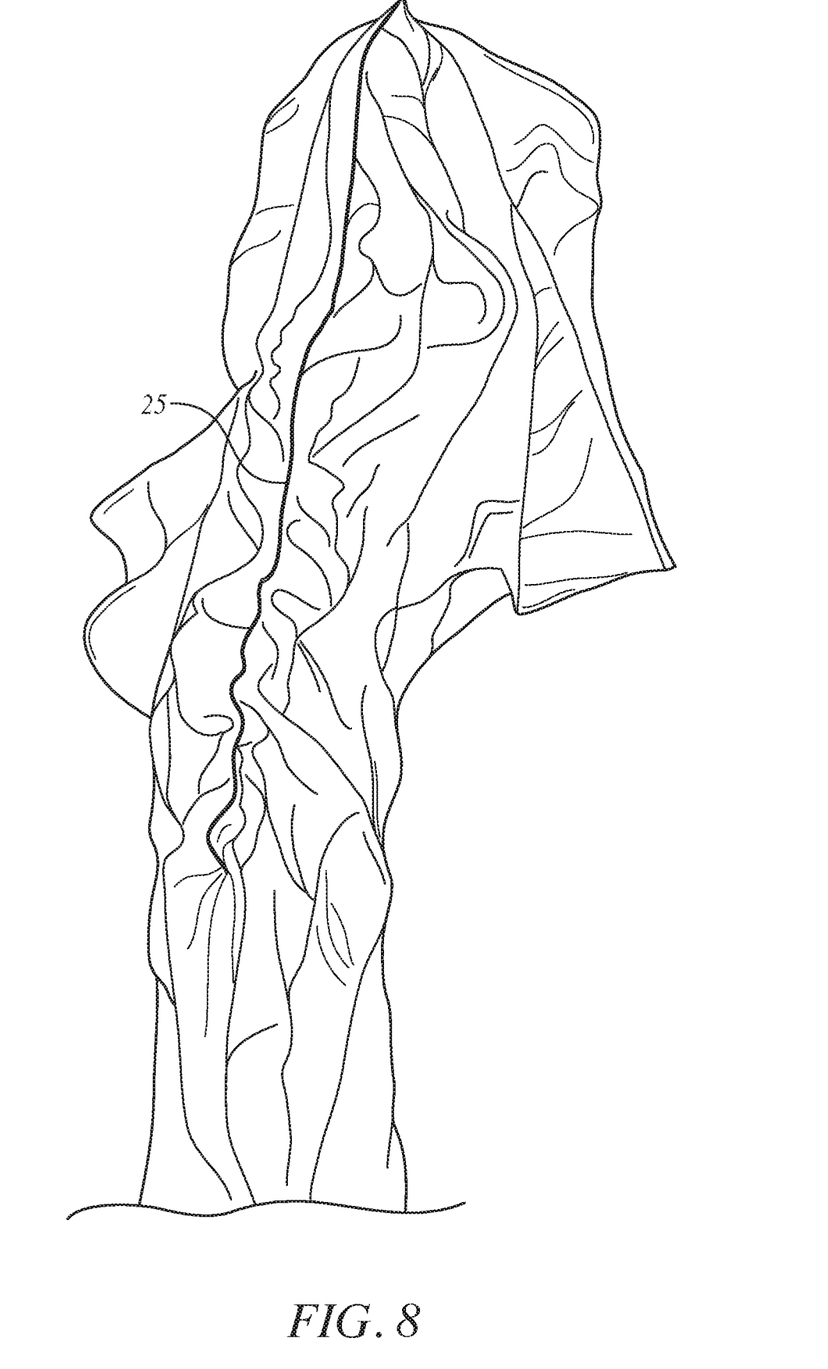
FIG. 8 is an isometric view of a hose seal in a closed position in which the elastic seal and snaps are hidden from view.

The unsealed area 1 and 6 of FIG. 1, the side openings 13A, 13B of FIGS. 2-5, the bottom openings 14A, 14B of FIGS. 2 and 3 and the bottom opening 14 of FIGS. 4-5 each constitute an "access area" when open for the introduction of pressurized conditioned air via an air hose from a source of such pressurized conditioned air. The open position of the access area is shown in FIGS. 6 and 7 and the closed position of the access area is shown in FIG. 8.

The unsealed area 1 of FIG. 1, the side openings 13A, 13B of FIGS. 2-5, the bottom openings 14A, 14B of FIGS. 2 and 3 and the bottom opening 14 of FIGS. 4-5 each constitute an "access area" when open for the introduction of pressurized conditioned air via an air hose from a source of such pressurized conditioned air. That is, the "access area" is opened to form an opening 21 by unsnapping snaps 22 to gain access to the flow areas 7 of FIGS. 1-5. An air discharge end of an air hose may be inserted into the opening 21. An elastic band 23, which is secured to the blanket about the periphery of the opening 21, may be stretched about the hose to help retain the air hose in its inserted position for discharging air into the flow areas 7.

The opening 21 may be closed by snapping closed the snaps 22. Once the snaps 22 are closed, the snaps 22 and the elastic band 23 may be positioned so they cannot be seen exteriorly as depicted in FIG. 8. Instead, all that can be seen is a fold line 25 that forms from the blanket fabric as a result of the closed snaps. Each snap includes to complementary snap elements that may separate from each or fasten to each other. Each snap is of conventional construction.

Figure 9:
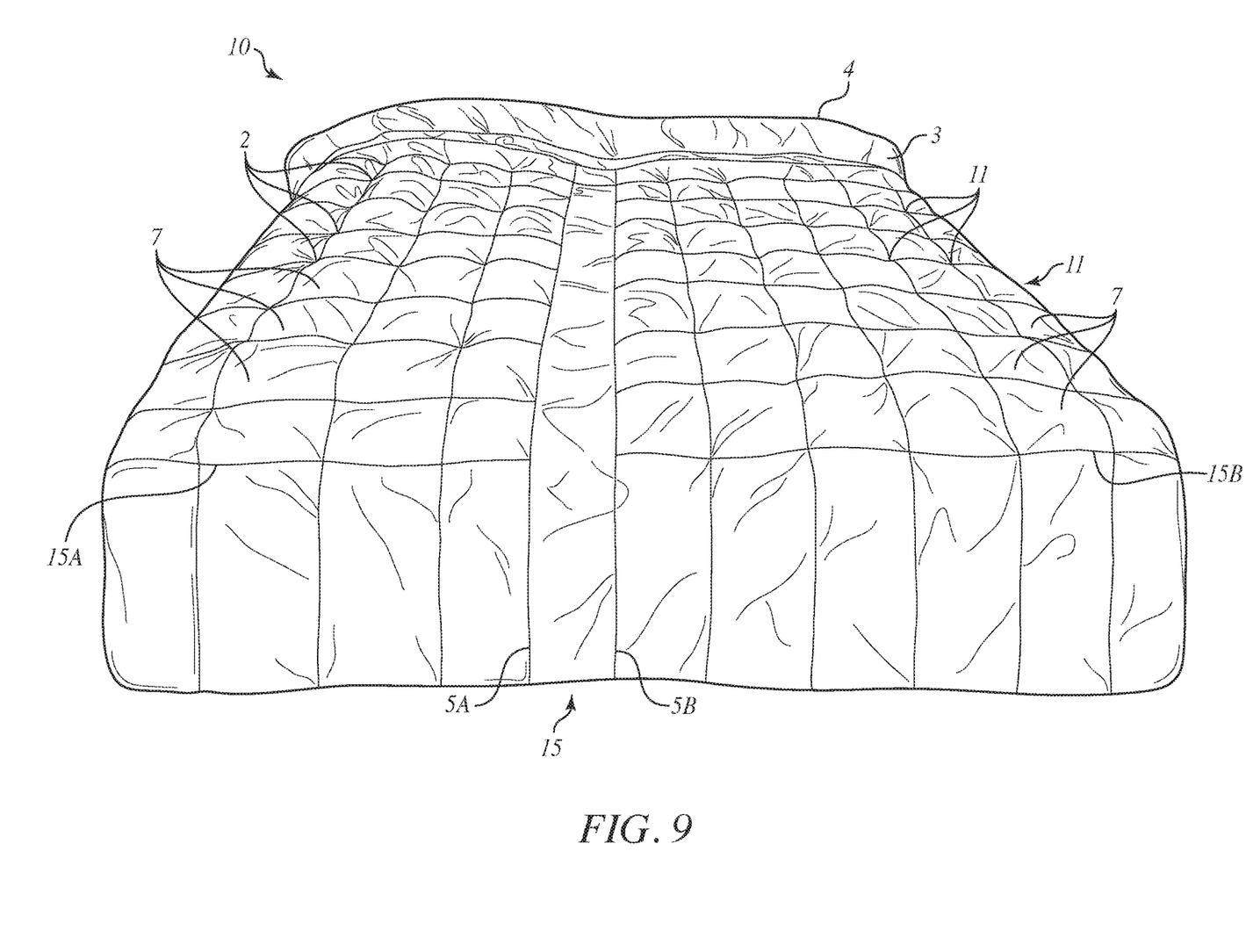
FIG. 9 is an isometric view of the further blanket of FIGS. 2 and 3 after inflation of the blanket.

Indeed, the user is given a choice of using either a side opening (1, 6, 13A, 13B of FIGS. 1-5 as applicable) or a bottom opening (14, 14A, 14B of FIGS. 1-5 as applicable) for the air hose. The side or bottom openings that are not used foe the air hose, therefore, may be closed by snapping closed the snaps 22, thereby hiding the elastic band 23 and the snaps 22 from view in the manner of FIG. 8. This hidden opening appearance is strongly preferred for multiple redundant access areas that may not be used at the same time. The result from inflation of the bed covering or blanket is shown in FIG. 9. As can be appreciated, the location of the tack stitches 2 in a uniform manner prevents giving rise to a ballooning effect.

Figure 10:
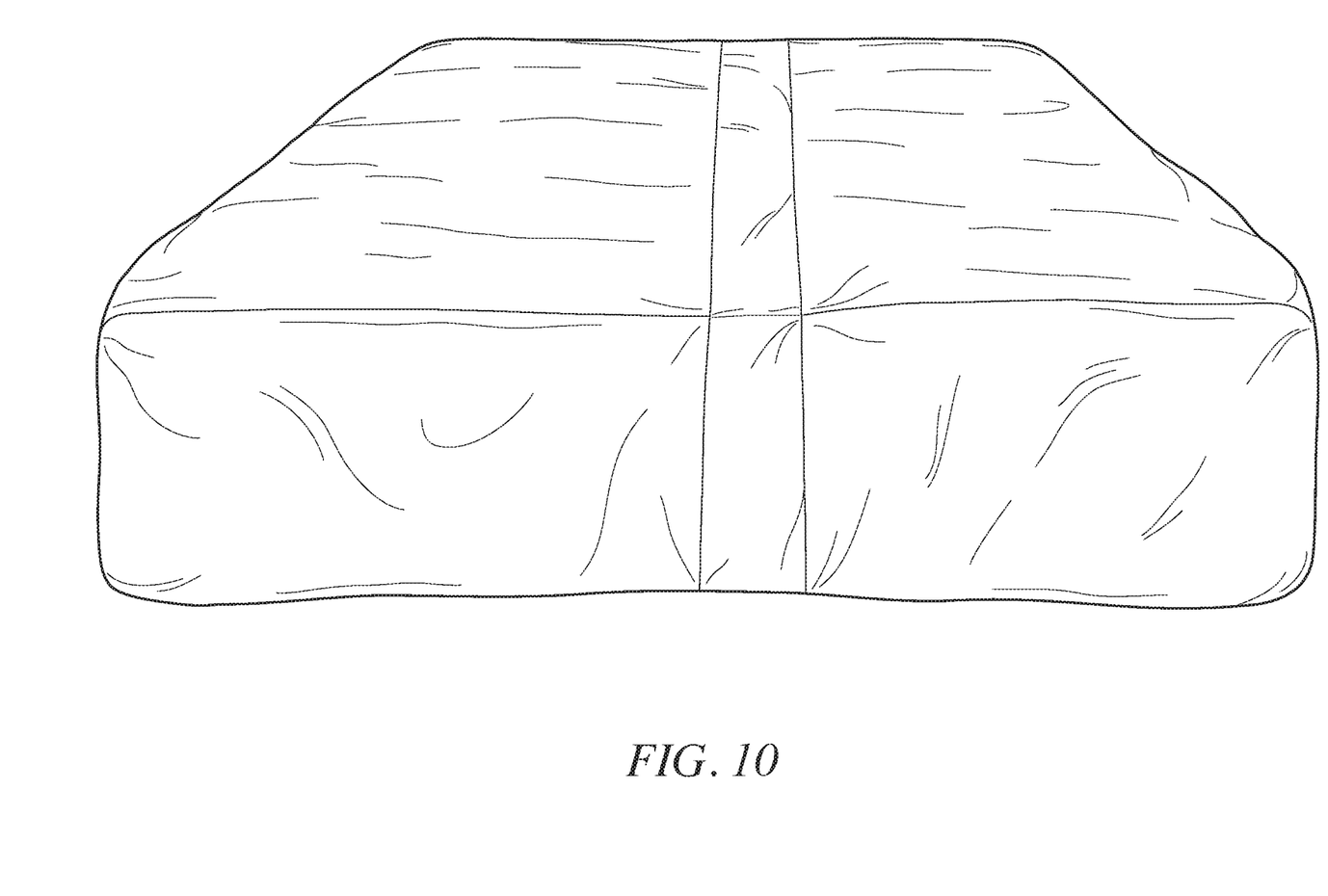
FIG. 10 is an isometric view of an additional blanket prior to inflation that lacks the joining elements of the further blanket of FIGS. 2 and 3.
Figure 11:
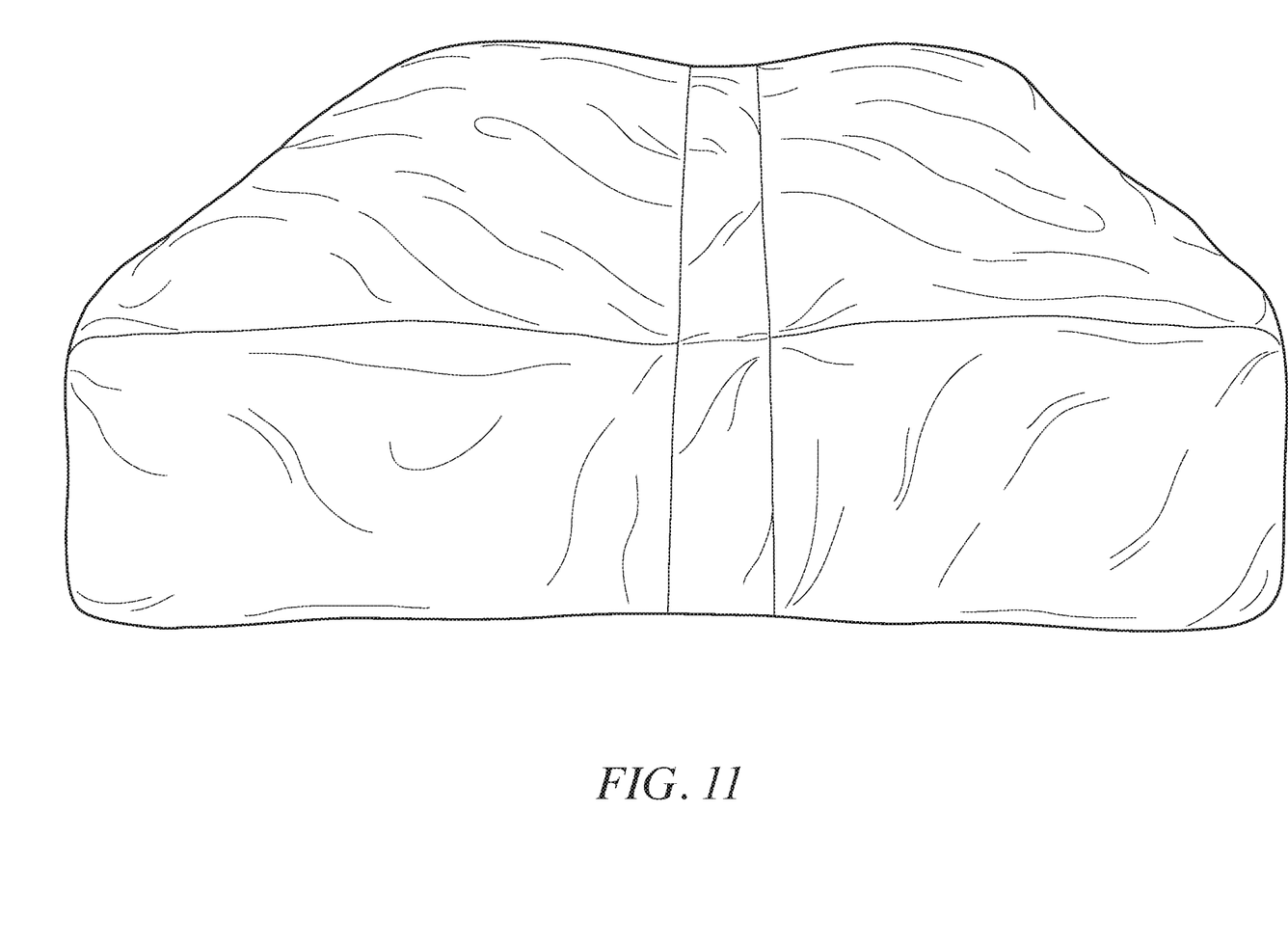
FIG. 11 is an isometric view of the additional blanket of FIG. 10 after inflation to illustrate a ballooning effect.

Turning to FIGS. 10 and 11, a simple sheet assembly with an interior air cavity is shown before and after its inflation, respectively. Indeed, the bed covering in FIG. 11 could be even more "balloony" than shown. Unlike the embodiments of the invention, there are no uniformly spaced apart joining means, such as thread stitches, to join together the plurality of sheets that comprising the bed covering. The presence of the thread stitches 2 of FIGS. 1-5 and 9 arranged in the uniform manner throughout the central region of the bed covering prevents the full ballooning effect of FIG. 11 from arising. The absence of such thread stitches, as in the bed covering of FIGS. 10 and 11, enables the ballooning effect to arise upon inflation of the internal airflow cavity. In practice this ballooning could result in a vertical inflation of more than 18 inches, which is very undesirable.

Figure 13:
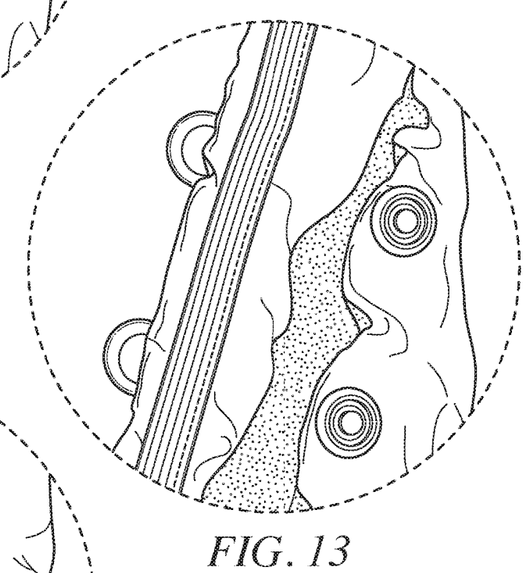
FIG. 13 is an enlarged view showing a portion of the air inlet prior to being closed by conventional snaps.

The conventional snaps 22 of FIG. 8 are also shown in the enlarged view of FIG. 13 and are arranged with its male and female parts arranged to be brought together to fasten with each other by a snap fit. A portion of the elastic band is also apparent in FIG. 13.

The conventional snaps 22 that may be used in accordance with the invention are exemplified by those suited for woven fabrics and those suited for knitted fabrics. Conventional snaps suited for woven fabrics include an S-spring type snap, whose socket (female part) incorporates a parallel spring mechanism that engages a stud (male part) with the spring resembling the shape of the letter S, and include a ring spring type snap, whose socket (female part) incorporates a single spring in the shape of a split ring that fits around the inside diameter of the socket to engage the stud (male part). Conventional snaps suited for knitted fabrics include a prong type snap, whose petal like socket (female) engages a stud (male). The prong type snap has a five-pronged ring that attaches to either the socket or the stud.

Figure 12:
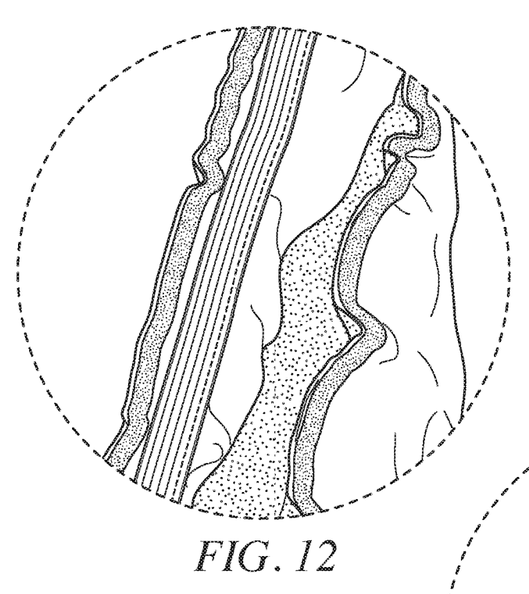
FIG. 12 is an enlarged view showing a portion of the air inlet prior to being closed by conventional strips of hooks and loops.

As an alternative to the snaps, conventional strips of hook and loop fasteners as shown in FIG. 12 may be used instead that engage each other to retain themselves upon contact and thereby close the air inlet yet can be manually pulled upon to release them from their engagement to open the air inlet from the closed condition. A portion of the elastic band is also apparent in FIG. 12.

Figure 14:
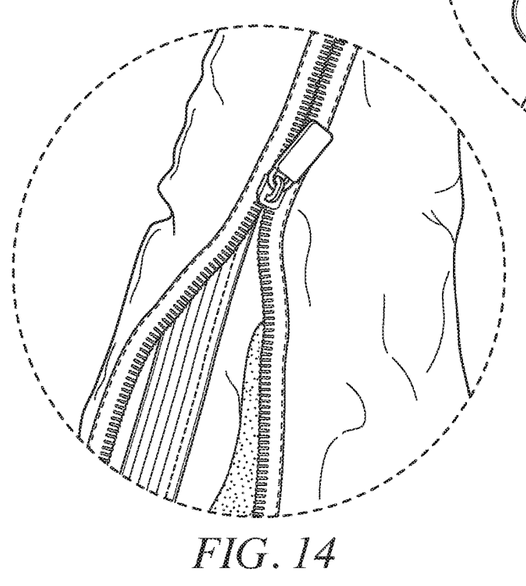
FIG. 14 is an enlarged view showing a portion of the air inlet being closed by a conventional zipper.

As a further alternative, a conventional zipper of FIG. 14 may be used instead whose zipper slide is pulled across the air inlet in one direction to close the air inlet with by engaging its zipper teeth to mesh with each other to fasten or is pulled in the opposite direction to open the air inlet by disengaging its zipper teeth which then unfasten. A portion of the elastic band is also apparent in FIG. 14.

US Patent Application Publication No. US 2015/0121620 A1 has disclosure for an air delivery outlet nozzle connected to a hose, which extends from a fan/blower discharge of a bedding climate control apparatus. Such disclosure is incorporated herein by reference. The nozzle has a central bend because of which the pressurized airflow entering from the hose changes direction along curvature of the bend. In accordance with the present invention, such an air delivery outlet nozzle is inserted in at least one air inlet of the bed covering so that the distal end portion of the air delivery outlet nozzle upstream of the bend rests upon a clear area of the bed covering that is clear of any joining elements.

As can be seen in FIGS. 2 and 4, the clear area is adjacent the at least one air inlet and lacks any of the joining elements. The clear area has a length that extends between the at least one air inlet and one of the joining elements and having a width that is bounded in part by another of the joining elements whose separation distance from the edge of the associated region is shorter than the length of the clear area. The air delivery outlet nozzle may be dispensed with entirely if desired and instead the distal end of the hose or of any kind of air conduit may replace it by resting upon the clear area instead.

While the foregoing description and drawings represent the preferred embodiments of the present invention, it will be understood that various changes and modifications may be made without departing from the scope of the present invention.

What is claimed is:

1. A bed covering apparatus, comprising:
a bedding material that is flexible and has a plurality of layers between which is an air cavity and having at least one air inlet in fluid communication with the air cavity, the plurality of layers and having folds;
at least one fastener that has respective components that complement each other so as to fasten to each other in response to being brought together to engage with each other and to unfasten from each other in response to being separated from each other to disengage from each other, the respective components of the at least one fastener being arranged to close the at least one air inlet while fastened to each other and being arranged to open the at least one air inlet while unfastened from each other, the at least one fastener being arranged at least partially concealed within the folds of the plurality of layers with the respective components are fastened to each other and the at least one air inlet closed, the at least one fastener being arranged to provide access to the at least one air inlet for delivery of forced airflow as the respective components are unfastened from each other to open the at least one air inlet; and
a plurality of joining elements that join together the plurality of layers, wherein the plurality of joining elements include multiple ones of the joining elements within confines of the bed covering within a quadrilateral area having right angles that is spaced from the at least one inlet, the bed covering having a further area of identical dimension to that of the quadrilateral area with right angles, the further area being adjacent the at least one air inlet and lacking any of the plurality of joining elements.

2. The bed covering apparatus of claim 1, wherein the at least one air inlet is bounded by an elastic band that imparts a resilient, elastic force upon being stretched.

3. The bed covering apparatus of claim 2, in combination with an air conduit that has a portion extending through the at least one air inlet, the elastic band stretching under tension around a periphery of the portion of the air conduit and thereby imparting the elastic force to retain the portion of the air conduit the air conduit, which is configured to pass forced air through the at least one air inlet as the portion extends through the at least one air inlet.

4. The bed covering apparatus of claim 3, wherein the portion of the air conduit is selected from the group consisting of an air delivery outlet nozzle and an air hose.

5. The bed covering apparatus of claim 1, wherein the at least one fastener is selected from the group consisting of at least one snap with a socket and a stud as the respective components, at least one pair of strips with hooks and loops as the respective components and at least one zipper having a slider with engaging teeth that mesh with each other as the respective components.

6. The bed covering apparatus of claim 1, wherein the respective components of the at least one fastener self-close with each other in response to manual force exerted in one direction upon being brought together and that disengage from each other in response to manual force exerted in a direction opposite the one direction to separate the respective components from each other.

7. The bed covering apparatus of claim 1, wherein the further area is bounded in part by a further joining element, the further joining element having a separation distance from one of a plurality of peripheral edges of the bed covering that is closest to the further joining element, the separation distance being shorter than a length of the quadrilateral area.

8. The bed covering apparatus of claim 1, wherein the bedding material is made of a fabric selected from the group consisting of woven fabric and knitted fabric.

9. The bed covering apparatus of claim 1, wherein the plurality of layers of the bedding material are thread stitched together with thread stitches.

10. The bed covering apparatus of claim 1, wherein the plurality of layers of the bedding material are joined together with tack stitches.

11. The bed covering apparatus of claim 1, wherein the plurality of layers of the bedding have different air permeability relative to each other.

12. The bed covering apparatus of claim 1, wherein the at least one fastener is fully hidden from view within the folds of the plurality of layers with the at least one air inlet closed by the at least one fastener.

13. The bed covering apparatus of claim 12, wherein the at least one fastener is selected from the group consisting of at least one snap with a socket and a stud as the respective components and at least one pair of strips with hooks and loops as the respective components as the respective components.

* * * * *